US009289414B2

(12) United States Patent
Arbiser

(10) Patent No.: US 9,289,414 B2
(45) Date of Patent: Mar. 22, 2016

(54) CARBAZOLE FORMULATIONS FOR THE TREATMENT OF PSORIASIS AND ANGIOGENESIS

(71) Applicant: Jack L. Arbiser, Atlanta, GA (US)

(72) Inventor: Jack L. Arbiser, Atlanta, GA (US)

(*) Notice: Subject to any disclaimer, the term of this patent is extended or adjusted under 35 U.S.C. 154(b) by 19 days.

(21) Appl. No.: 13/956,170

(22) Filed: Jul. 31, 2013

(65) Prior Publication Data

US 2013/0338207 A1    Dec. 19, 2013

Related U.S. Application Data

(63) Continuation of application No. 11/154,780, filed on Jun. 16, 2005.

(60) Provisional application No. 60/580,050, filed on Jun. 16, 2004.

(51) Int. Cl.
| | |
|---|---|
| *A61K 31/403* | (2006.01) |
| *A61K 9/107* | (2006.01) |
| *A61K 9/06* | (2006.01) |
| *A61K 31/55* | (2006.01) |
| *A61K 31/675* | (2006.01) |
| *A61K 31/695* | (2006.01) |

(52) U.S. Cl.
CPC ............. *A61K 31/403* (2013.01); *A61K 9/06* (2013.01); *A61K 9/107* (2013.01); *A61K 31/55* (2013.01); *A61K 31/675* (2013.01); *A61K 31/695* (2013.01)

(58) Field of Classification Search
CPC ... A61K 31/403; A61K 31/55; A61K 31/675; A61K 31/695; A61K 9/107; A61K 9/06
See application file for complete search history.

(56) References Cited

U.S. PATENT DOCUMENTS

| | | |
|---|---|---|
| 3,956,295 A | 5/1976 | Biere et al. |
| 4,818,759 A | 4/1989 | Charping |
| 4,822,811 A | 4/1989 | Summers |
| 5,135,920 A | 8/1992 | Kanamaru et al. |
| 5,382,582 A | 1/1995 | Chan |
| 5,698,586 A | 12/1997 | Kishimoto et al. |
| 5,710,136 A | 1/1998 | Robinson et al. |
| 5,720,954 A | 2/1998 | Hudziak et al. |
| 5,731,294 A | 3/1998 | Robinson et al. |
| 5,783,404 A | 7/1998 | Koski |
| 5,801,156 A | 9/1998 | Robinson et al. |
| 5,814,315 A | 9/1998 | Hung et al. |
| 6,337,337 B1 | 1/2002 | Buck |
| 6,486,152 B1 | 11/2002 | Coles et al. |
| 7,179,493 B2 | 2/2007 | Ellison et al. |
| 2002/0065266 A1* | 5/2002 | Jensen et al. ............ 514/213.01 |
| 2002/0198192 A1 | 12/2002 | Keren |
| 2006/0003966 A1 | 1/2006 | Arbiser |

FOREIGN PATENT DOCUMENTS

| | | |
|---|---|---|
| FR | 2753098 A1 | 3/1998 |
| GB | 1020613 A | 2/1966 |
| WO | 0069794 A2 | 11/2000 |
| WO | 0155108 A2 | 8/2001 |
| WO | 02060867 A2 | 8/2002 |

OTHER PUBLICATIONS

Mar. 7, 2008 Office Action in U.S. Appl. No. 11/154,780.
Apr. 14, 2009 Office Action in U.S. Appl. No. 11/154,780.
Jun. 9, 2010 Office Action in U.S. Appl. No. 11/154,780.
Jul. 6, 2012 Answer to Appeal Brief in U.S. Appl. No. 11/154,780.
Jul. 27, 2011 Office Action in U.S. Appl. No. 11/154,780.
Oct. 2, 2008 Office Action in U.S. Appl. No. 11/154,780.
Oct. 5, 2009 Office Action in U.S. Appl. No. 11/154,780.
Arbiser, J., et al., "Carbazole is a Naturally Occurring Inhibitor of Angiogenesis and Inflammation Isolated from Antipsoriatic Coal Tar", "Journal of Investigative Dermatology", Apr. 13, 2006, pp. 1396-1402, vol. 126.
Arbiser, J., et al., "The antiangiogenic agents TNP-470 and 2-methoxyestradiol inhibit the growth of angiosarcoma in mice", "J. Am. Acad. Dermatol.", Jun. 1999, pp. 925-929, vol. 40.
Bai, X., et al., "Honokiol, a Small Molecular Weight Natural Product, Inhibits Angiogenesis in Vitro and Tumor Growth in Vivo", "The Journal of Biological Chemistry", Sep. 12, 2003, pp. 35501-35507, vol. 278, No. 37.
Campbell, T., et al., "Dimorphic Cutaneous Manifestation of a Toxic Eruption Due to Erlotinib Therapy", "Journal of Drugs in Dermatology", Dec. 2008, pp. 1161-1163, vol. 7, No. 12.
Chen, B., et al., "Essential Rold of Mitogen-Activated Protein Kinase Pathway and c-Jun Induction in Epidermal Growth Factor-Induced Gene Expression of Human 12-Lipoxygenase", "Molecular Pharmacology", 2000, pp. 153-161, vol. 57.
Creamer, D., et al., "Angiogenesis in psoriasis", "Angiogenesis", 2002, pp. 231-236, vol. 5.
Degreef, H., et al., "A double-blind vehicle-controlled study of R 68 151 in psoriasis: A topical 5-lipoxygenase inhibitor", "Journal American Academy of Dermatology", May 1990, pp. 751-755, vol. 5, No. 1.
Disdier, B., et al., "Analysis by GC-MS of Polycyclic Aromatic Hydrocarbons in a Cream Containing Coal Tar", "Polycyclic Aromatic Compounds", 2000, pp. 169-177, vol. 20.
Fan, T., et al., "Controlling the vasculature: angiogenesis, antiangiogenesis and vascular targeting of gene therapy", "TiPS", Feb. 1995, pp. 57-66, vol. 16.
U.S. Food and Drug Administration, "Labeling of drug products for the control of dandruff, seborrheic dermatitis, or psoriasis", "21 CFR Ch. 1 Section 358.750", Apr. 1, 2002, pp. 302-303.
Finch, P., et al., "Altered Expression of Keratinocyte Growth Factor and Its Receptor in Psoriasis", "American Journal of Pathology", Dec. 1997, pp. 1619-1628, vol. 151, No. 6.
Folkman, J., "Angiogenesis in cancer, vascular, rheumatoid and other disease", "Nature Medicine", 1995, pp. 27-30 (Abstract), vol. 1.

(Continued)

*Primary Examiner* — Kyle Purdy
(74) *Attorney, Agent, or Firm* — Andrews Kurth LLP; David Bradin

(57) ABSTRACT

The methods and compositions disclosed herein relate to using carbazole, and derivatives thereof to modify a signaling activity such as epidermal growth factor receptor (EGFR) signalling, and angiogenesis activity, in a cell.

7 Claims, 5 Drawing Sheets

(56) References Cited

OTHER PUBLICATIONS

Herman, S., et al., "Low dose methotrexate induces apoptosis with reactive oxygen species involvement in T lymphocytic cell ines to a greater extent than in monocytic lines", "Inflamm. res.", Jul. 2005, pp. 273-280, vol. 54.

Hollstein, M., et al., "Quinoline: Conversion to a Mutagen by Human and Rodent Liver", "J. Natl. Cancer Inst.", Feb. 1978, pp. 405-410, vol. 60, No. 2.

Huang, C., et al., "Ornithine decarboxylase prevents methotrexate-induced apoptosis by reducing intracellular reactive oxygen species production", "Apoptosis", Aug. 2005, pp. 895-907, vol. 10.

Hultqvist, M., et al., "A New Arthritis Therapy with Oxidative Burst Inducers", "PLoS Medicine", Sep. 12, 2006, pp. 1625-1636, vol. 3, No. 9.

World Health Organization International Agency for Research on Cancer, "Coal-tars", "IARC Monographs Supplement 7", 1987, pp. 175-176.

World Health Organization International Agency for Research on Cancer, "Carbazole", "IARC Monographs on the Evaluation of Carcinogenic Risks to Humans: Re-evaluation of Some Organic Chemicals, Hydrazine and Hydrogen Peroxide", 1999, pp. 1319-1323, vol. 71.

Kleinsmith, L, et al., "Understanding Cancer and Related Topics: Understanding Angiogenesis", "Understanding Cancer Series: Angiogenesis", Jan. 28, 2005, pp. 1-28 (Accessed via http://www.cancer.gov/cancertopics/understandingcancer/angiogenesis), Publisher: National Cancer Institute.

Mascia, F., et al., "Blockade of the EGF Receptor Induces a Deranged Chemokine Expression in Kreatinocytes Leading to Enhanced Skin Inflammation", "American Journal of Pathology", Jul. 2003, pp. 303-312, vol. 163, No. 1.

Mukhtar, H., et al., "Skin tumor initiating activity of therapeutic crude coal tar as compared to other polycyclic aromatic hydrocarbons in SENCAR mice", "Cancer Letters", May 1986, pp. 147-151 (Abstract), vol. 31, No. 2.

Oh, I., "TPA (12-O-tetradecanoyl-phorbol-13-acetate) as a carcinogen for mouse skin. A positive dose-response relationship", "Virchows Arch B Cell Pathol Incl Mol Pathol", 1985, pp. 129-135 (Abstract), vol. 49, No. 2.

Peters, C., et al., "Coal Tar Dissolution in Water-Miscible Solvents: Experimental Evaluation", "Environ. Sci. Technol.", 1993, pp. 2831-2843, vol. 27.

Rasmussen, K., et al., "Mutagenicities of Hydroxy-substituted Carbazoles and Dibenzothiophenes Using the CHO/HGPRT Assay", "Environmental Toxicology and Chemistry", 1991, pp. 1133-1137, vol. 10.

Resnick, S., et al., "Oxidation of carbazole to 3-hydroxycarbazole by naphthalene 1,2-dioxygenase and biphenyl 2,3-dioxygenase", "FEMS Microbiology Letters", 1996, pp. 297-302, vol. 113.

Smith, K., et al., "Accidental Success with Carbamazepine for Psoriatic Erythroderma", "New English Journal of Medicine", Dec. 26, 1996, pp. 1999-2000, vol. 335, No. 26.

Tabka, T., et al., "Etude de la cytotoxicite in vitro de derives du carbazole I. Nitro et amino-9H-carbazoles", "Eur. J. Med. Chem.", 1988, pp. 119-124 (English Abstract), vol. 23.

Tabka, T., et al., "Etude de la cytotoxicite in vitro de derives du carbazole II. Nitro et amino halogeno-6 dimethyl-1,4 9H-carbazoles", "Eur. J. Med. Chem.", 1989, pp. 605-610 (English Abstract), vol. 24.

Public Health Service Agency for Toxic Substances and Disease Registry, "Toxicological Profile for Wood Creosote, Coal Tar Creosote, Coal Tar, Coal Tar Pitch, and Coal Tar Pitch Volatiles", Sep. 2002, pp. 1-354 and A1-D3, Publisher: U.S. Dept. Health and Human Services.

Van Der Kerkhof, P., et al., "Topical R-85355, a Potent and Selective 5-Lipoxygenase Inhibitor, Fails to Improve Psoriasis", "Skin Pharmacol", 1996, pp. 307-311, vol. 9.

Veldhoen, M., et al., "Natural agonists for aryl hydrocarbon receptor in culture medium are essential for optimal differentiation of Th17 T cells", "J. Exp. Med.", Dec. 29, 2008, pp. 43-49, vol. 206, No. 1.

World Health Organization International Agency for Research on Cancer, "Polynuclear Aromatic Compounds, Part 4, Bitumens, Coal-tars and Derived Products, Shale-oils and Soots", Apr. 20, 1998, pp. 39-40, 83-85, 161-163, 219-220, vol. 35.

Zorzou, M., et al., "Exacerbation of Psoriasis after Treatment with an EGFR Tyrosine Kinase Inhibitor", "Acta Derm Venereol", Jul. 2004, pp. 308-336, vol. 84.

\* cited by examiner

CARBAZOLE FORMULATIONS FOR THE TREATMENT OF PSORIASIS AND ANGIOGENESIS

CROSS-REFERENCE TO RELATED APPLICATION

This application is a continuation under 35 U.S.C. 120 of U.S. application Ser. No. 11/154,780, filed Jun. 16, 2005, which in turn claims the benefit of priority of U.S. Ser. No. 60/580,050, filed Jun. 16, 2004, entitled "Carbazole Formulations for the Treatment of Angiogenesis," the teachings of which are expressly incorporated herein by reference for all purposes.

STATEMENT REGARDING FEDERALLY SPONSORED RESEARCH

The U.S. government has certain rights in this invention by virtue of NIAMS Grants RO3AR44947 to J. L. Arbiser, Emory Skin Disease Research Core Center P30 AR 42687 and RO1 47901 to J. L. Arbiser.

FIELD OF THE INVENTION

The invention is generally in the field of methods and compositions for inhibiting angiogenesis and signal transduction.

BACKGROUND OF THE INVENTION

Psoriasis is a common inflammatory condition found in 1-2% of the population. Mild psoriasis is treated with primarily topical glucocorticoids, and other topical agents such as vitamin D and topical retinoids having a smaller role due to decreased efficacy. Severe psoriasis is often treated with systemic medications, including methotrexate, cyclosporine, and retinoids, and more recently with biological agents, such as soluble receptors to tumor necrosis factor α (TNFα), or antibodies to TNFα receptors. While these therapies are effective under some settings, all of them are associated with side effects. Hepatotoxicity is a major issue for long-term use of methotrexate and retinoids, while hypertension, nephropathy and systemic immunosuppression complicate the use of cyclosporine. Thus, there is a pressing need for effective topical therapies for psoriasis, especially those working through mechanisms that differ from those currently available.

The epidermal growth factor receptor (EGFR) is a cell membrane growth factor receptor. Aberrant signaling through the EGFR appears to be associated with angiogenesis. Normal angiogenesis plays an important role in a variety of processes including embryonic development, wound healing and several components of female reproductive function. However, undesirable or pathological angiogenesis has been associated with disease states including diabetic retinopathy, psoriasis, cancer, rheumatoid arthritis, atheroma, Kaposi's sarcoma and haemangioma (Fan et al (1995) Trends Pharmacol, 16: 57-66; Folkman (1995) Nat. Med. 1: 27-31). Development of effective preventive and treatment means has been hampered by inadequate understanding of the factors controlling this process.

Accordingly, a need exists for methods of treating a mammal having a disease or condition characterized by increased angiogenesis or aberrant EGFR signaling.

SUMMARY OF THE INVENTION

The present invention is based, in part, on the discovery that carbazole isolated from coal tar, exhibits signal transduction regulating activity, (e.g., epidermal growth factor receptor (EGFR) regulating activity), as well as angiogenesis modulating activity.

In one aspect, the invention pertains to a method for treating disorders characterized by elevated, or aberrant signaling (e.g., elevated levels of epidermal growth factor, or aberrant epidermal growth factor receptor signaling), comprising administering an effective amount of a carbazole, or a derivative thereof, having the general formula:

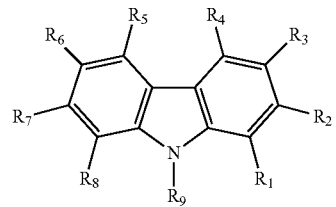

wherein, $R_1$-$R_9$ can be a hydrogen atom, halogen atom, alkyl group, trihaloalkyl group, alkenyl group, alkynyl group, cycloalkyl group, cycloalkenyl group, amino group, aryl group, substituted aryl, heteroaryl group, heterocycloalkyl group, heterocycloalkenyl group, heteroalicyclic group, hydroxyl group, alkoxy group, cycloalkoxy group, aryloxy group, heteroaryloxy group, heteroalicycloxy group, thiohydroxy group, thioalkyoxy group, thiocycloalkoxy group, thioheteroaryloxy group, thioheteroalicycloxy group, cyano group, carbamyl group, C—O-carbamyl group, N-carbamyl group, O-thiocarbamyl group, N-thiocarbamyl group, silyl group, phosphonyl group, C-carboxy group, O-carboxy group, N-amido group, C-amido group, sulfinyl group, sulfonyl group, S-sulfonamido group, N-sulfonamido group, trihalomethanesulfonyl group, guanyl group, guanidine group, and trihalomethanesulfonamido group.

The disorder may further be characterized by angiogenesis. In one embodiment, $R_1$-$R_9$ groups of the carbazole are all hydrogen atoms. In another embodiment, the carbazole can be hydroxylated, oxidized, or halogenated. Exemplary hydroxylated carbazoles can be selected from the group consisting of 2-hydroxy-carbazole, 3-hydroxy-carbazole, 4-hydroxy-carbazole, 2,2-hydroxy-carbazole, and 2,4-hydroxy-carbazole. In yet another embodiment, the carbazole is carbamazepine.

The carbazole can also be formulated in a pharmaceutically acceptable carrier for topical administration. The carrier can be selected from the group consisting of ointments, gels, lotions, sprays, shampoos, powders, foams, and solutions, and the carbazole can be present in the carrier at a concentration of about 1-20% by weight.

The carbazole can be used to treat any disorder characterized by elevated levels of angiogenesis or aberrant signaling (e.g., aberrant epidermal growth factor receptor signaling). Examples of such disorders include skin disorders such as psoriasis, acne, rosacea, and eczema. In one embodiment, the skin disorder is psoriasis.

The methods and compositions of the invention can also be used to modulate a pathway (e.g., a rac pathway), or a step in a pathway, associated with skin disorders. The modulation can result in an amelioration and/or treatment of the disorders associated with the pathway.

Accordingly, in another aspect, the invention pertains to a method for treating disorders associated with a rac signaling pathway, comprising administering an effective amount of carbazole or a derivative thereof having the general formula described above.

In yet another aspect, the invention pertains to a pharmaceutically acceptable carbazole formulation, comprising an effective amount of purified carbazole, or a derivative thereof, having the general formula:

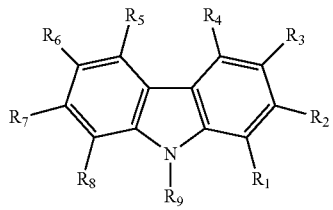

wherein, $R_1$-$R_9$ can be a hydrogen atom, halogen atom, alkyl group, trihaloalkyl group, alkenyl group, alkynyl group, cycloalkyl group, cycloalkenyl group, amino group, aryl group, heteroaryl group, heteroalicyclic group, hydroxyl group, alkoxy group, cycloalkoxy group, aryloxy group, heteroaryloxy group, heteroalicycloxy group, thiohydroxy group, thioalkyoxy group, thiocycloalkoxy group, thioheteroaryloxy group, thioheteralicycloxy group, cyano group, carbamyl group, C—O-carbamyl group, N-carbamyl group, O-thiocarbamyl group, N-thiocarbamyl group, silyl group, phosphonyl group, C-carboxy group, O-carboxy group, N-amido group, C-amido group, sulfinyl group sulfonyl group S-sulfonamido group, N-sulfonamido group, trihalomethanesulfonyl group, guanyl group, guanidine group, trihalomethanesulfonamido group; and a pharmaceutically acceptable carrier.

DETAILED DESCRIPTION OF THE INVENTION

Figure 1:
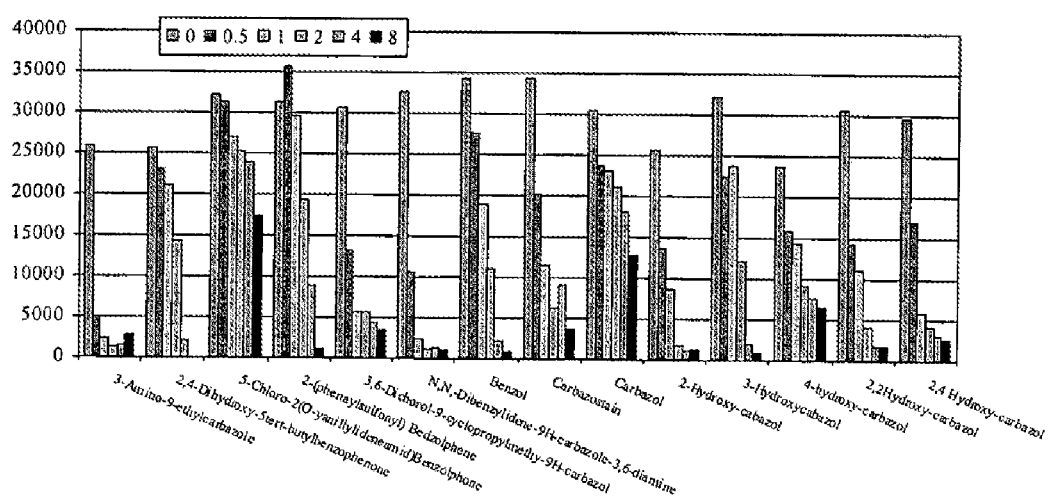
FIG. 1 is a bar graph which demonstrates the effect of carbazole and carbazole derivatives on the proliferation of transformed murine endothelial cells. The graph shows concentration of drug (μl/ml) versus cell growth (total cell number)

Certain exemplary embodiments of the invention will now be described to provide an overall understanding of the principles of the structure, function, manufacture, and use of the methods and compositions disclosed herein. Those skilled in the art will understand that the methods and compositions specifically described herein are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In one aspect, the invention pertains to using a carbazole to modulate signal transduction activity (e.g., epidermal growth factor receptor (EGFR) activity) and/or angiogenesis activity. Carbazole and derivatives or analogs thereof, having the general formula as shown and discussed below, are useful in the treatment of angiogenesic mediated disorders. As used herein, the term "carbazole" includes carbazole and derivatives and analogs thereof.

Carbazole and carbazole derivatives or analogs have the following general structure:

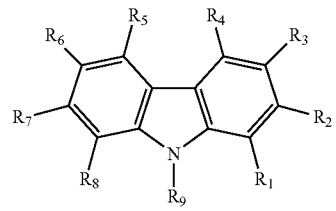

wherein, $R_1$-$R_9$ can be a hydrogen atom, halogen atom, alkyl group, trihaloalkyl group, alkenyl group, alkynyl group, cycloalkyl group, cycloalkenyl group, amino group, aryl group, substituted aryl, heteroaryl group, heterocycloalkyl group, heterocycloalkenyl group, heteroalicyclic group, hydroxyl group, alkoxy group, cycloalkoxy group, aryloxy group, heteroaryloxy group, heteroalicycloxy group, thiohydroxy group, thioalkyoxy group, thiocycloalkoxy group, thioheteroaryloxy group, thioheteroalicycloxy group, cyano group, carbamyl group, C—O-carbamyl group, N-carbamyl group, O-thiocarbamyl group, N-thiocarbamyl group, silyl group, phosphonyl group, C-carboxy group, O-carboxy group, N-amido group, C-amido group, sulfinyl group, sulfonyl group, S-sulfonamido group, N-sulfonamido group, trihalomethanesulfonyl group, guanyl group, guanidine group, and trihalomethanesulfonamido group. Carbazole has the structure wherein $R_1$-$R_9$ are all hydrogen.

Particularly useful derivatives of carbazole include hydroxylated derivatives of carbazole such as 2-hydroxycarbazole, 3-hydroxy-carbazole, 4-hydroxy-carbazole, 2,2-hydroxy-carbazole, and 2,4-hydroxycarbazole. Other exemplary derivatives include, but are not limited to, 3,6 dichloro-9-cyclopropylmethylcarbazole; 3-amino-9-ethylcarbazole; and N,N-dibenzylidene-9H-carbazole-3,6-diamine. Derivatives and analogs of carbazole can be derived using standard organic chemistry methods.

Disorders or diseases that can be treated with the carbazole compounds include those mediated by angiogenesis and/or aberrant signaling (e.g., aberrant epidermal growth factor receptor (EGFR) signaling).

Such diseases include many different types of cancer including non-small cell lung cancer ("NSCLC"), cancer of head and neck, esophagus, stomach, large intestine, brain, small intestine, rectum, anus, gall bladder, kidney, bladder, liver, ureter, penis, vulva, breast, cervix, colon, prostate, ovaries; hematologic malignancies including leukemia and lymphoma; and malignant skin diseases including angiosarcoma, hemangioendothelioma, basal cell carcinoma, squamous cell carcinoma, malignant melanoma and Karposi's sarcoma.

Non-malignant diseases or conditions characterized by angiogenesis that may be treated include psoriasis, lymphangiogenesis, hemangioma of childhood, Sturge-Weber syndrome, verruca vulgaris, neurofibromatosis, tuberous sclerosis, pyogenic granulomas, recessive dystrophic epidermolysis bullosa, venous ulcers, acne, rosacea, eczema, molluscum contagiosum, seborrheic keratosis, and actinic keratosis.

Carbazole and its derivatives can also be used for the treatment of inflammatory disorders such as inflammatory bowel disease, arthritis, multiple sclerosis, lupus, and sarcoidosis.

The carbazole may be administered orally, buccally, parenterally, by inhalation spray, rectally, intradermally, transdermally, or topically in dosage unit formulations containing conventional nontoxic pharmaceutically acceptable carriers, adjuvants, and vehicles as desired. The term parenteral as used herein includes subcutaneous, intravenous, intramuscular, or intrasternal injection, and infusion techniques.

In another embodiment, the composition is administered orally or intravenously for treatment and/or prevention of different types of cancer or non-malignant diseases characterized by angiogenesis or aberrant signaling (e.g., aberrant EGFR signaling). Intravesical or intraperitoneal administration may also be used, depending on the type of disease. The carbazole compositions may also be provided in the form of carbazole containing wafers and biodegradable implants.

The carbazole compounds discussed herein, or pharmaceutically acceptable salts thereof, can be formulated as pharmaceutical compositions, including their polymorphic variations. As noted above, such compositions can be administered orally, buccally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrastemal injection, or infusion techniques. In an exemplary embodiment, the composition is administered topically.

Formulation of drugs is discussed in, for example, Hoover, John E., Remington's Pharmaceutical Sciences, (1975), Mack Publishing Co., Easton, Pa.; and Liberman, H. A. and Lachman, L., (1980) Eds., Pharmaceutical Dosage Forms, Marcel Decker, New York, N.Y. The term "pharmaceutically acceptable salt" means those salts which retain the biological effectiveness and properties of the compounds used in the present invention, and which are not biologically or otherwise undesirable. Such salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives, for example carboxylic acid amides, including carboxamides, lower alkyl carboxamides, di(lower alkyl)carboxamides, may be used.

The compounds (or pharmaceutically acceptable salts thereof) may be administered per se or in the form of a pharmaceutical composition wherein the active compound(s) is in admixture or mixture with one or more pharmaceutically acceptable carriers, excipients or diluents. Pharmaceutical compositions may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

The compounds may be complexed with other agents. The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); or lubricants (e.g., magnesium stearate or Sterotes); or a glidant such as colloidal silicon dioxide. If any such formulated complex is water-soluble, then it may be formulated in an appropriate buffer, for example, phosphate buffered saline or other physiologically compatible solutions. Alternatively, if the resulting complex has poor solubility in aqueous solvents, then it may be formulated with a non-ionic surfactant such as Tween, or polyethylene glycol. Thus, the compounds and their physiologically acceptable solvates may be formulated for administration.

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide surfactants including ionic and non-ionic detergents, and polyethylene glycols can be used. Mixtures of solvents and wetting agents such as those discussed above are also useful.

The compounds may also be formulated in rectal compositions such as suppositories or retention enemas, e.g., containing conventional suppository bases such as cocoa butter or other glycerides. Suppositories for rectal or vaginal administration of the compounds discussed herein can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal or vaginal temperature, and which will therefore melt in the rectum or vagina and release the drug.

Solid dosage forms for oral administration may include capsules, tablets, pills, powders, and granules. In such solid dosage forms, the compounds of this invention are ordinarily combined with one or more adjuvants appropriate to the indicated route of administration. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

Alternatively, for oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid) and sweetening, flavoring, and perfuming agents.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The amount of active ingredient that can be combined with the carrier materials to produce a single dosage form will vary depending upon the patient and the particular mode of administration.

Preparations for oral administration may be suitably formulated to give controlled release of the active compound. For administration by inhalation, the compounds may be delivered in the form of an aerosol spray or dry powder inhaler.

Dragee cores can be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in a conventional manner.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active compound(s) may be in powder form for constitution with a suitable vehicle, e.g., sterile pyrogen-free water, before use.

In addition to the formulations described previously, the compounds may also be formulated as a depot or sustained-release preparation. Such long acting formulations may be administered by implantation, osmotic pump or transcutaneous delivery (for example subcutaneously or intramuscularly), intramuscular injection or a transdermal patch. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

For topical application, the compound is combined with a carrier so that an effective dosage is delivered, based on the desired activity, at the site of application. The topical composition can be applied to the skin for treatment of diseases such as psoriasis. The carrier may be in the form of an ointment, cream, gel, shampoo, paste, foam, aerosol, suppository, pad or gelled stick. A topical composition for use of an ointment or gel consists of an effective amount of compound in an ophthalmically acceptable excipient such as buffered saline, mineral oil, vegetable oils such as corn or arachis oil, petroleum jelly, Miglyol 182, alcohol solutions, or liposomes or liposome-like products.

The formulation is administered as required to alleviate the symptoms of the disorder. Assays can be performed to determine an effective amount of the agent, either in vitro and in vivo. Representative assays are described in the examples provided below. Other methods are known to those skilled in the art, and can be used to determine an effective dose of these and other agents for the treatment and prevention of diseases or other disorders as described herein.

For the treatment of skin disorders, the carbazole compounds can be administered topically or regionally. In a preferred embodiment, the compounds are administered in an ointment, salve or other pharmaceutically acceptable carrier. For treatment of certain disorders characterized by elevated levels of EGFR, the carbazole compounds is applied topically in diseases or pathologic conditions of the skin, or locally in other tissues, to treat cancer, pre-malignant conditions and other diseases and conditions in which angiogenesis occurs. An exemplary administration technique is to apply the carbazole topically, such as an ointment, lotion, gel, spray, powder, shampoo, or solution, in an amount effective to inhibit epidermal growth factor receptor. An effective amount of the carbazole can be in the range of about 1-20% by weight, preferably about 1-10%, and most preferably about 1-5% of the carbazole. A composition containing about 1% carbazole can also be used. Suitable formulations can be administered periodically, such as about 1-3, or more times daily, for a period of time effective to alleviate the symptoms of the disorder. Treatments can continue until clinical improvement of the disorder is noted, for example from about 0-6 months. Clinical improvement can be manifested in decreased redness, thickness of plaques, decreased scaling, decreased area of involvement, or clearing of plaques. In addition, to treat a skin disorder such as psoriasis, the carbazole may be delivered for a period of time to improve the severity PASI (psoriasis area and severity index) score.

The composition may also be administered orally or intravenously for treatment and/or prevention of different types of cancer including cancer of head and neck, esophagus, stomach, large intestine, small intestine, rectum, anus, gall bladder, liver, kidney, bladder, ureter, penis, vulva, breast, cervix, or hematologic malignancies including leukemia and lymphoma. Intravesical administration could be used for prevention/treatment of bladder cancer, and intraperitoneal administration in a suitable vehicle could be employed for intraperitoneal malignancies, including ovarian cancer. Carbazole-containing wafers and biodegradable implants may be designed for use in treating brain tumors, in a manner similar to gliadel wafers.

Doses for oral administration of small molecule EGFR inhibitors can typically be in the range of about 50-700 gm/day. The dosage may be administered once per day or several or multiple times per day. The amount of the compound administered will be dependent on the subject being treated, the severity of the affliction, the manner of administration and the judgment of the prescribing physician.

The present invention will be further understood by reference to the following non-limiting examples.

EXAMPLES

Example 1

Identification of Active Ingredient in Coal Tar

Liquid extract of coal tar was concentrated under vacuum to get crude extract (20.0 mg). This extract was applied on a Sephadex LH 20 (3.0×100 cm) column and eluted with MeOH. The elution was monitored by TLC and similar fractions are combined to get 11 fractions. This fraction was assayed for inhibition of SVR cell viability (Arbiser et al. (1999) J. Am. Acad. Dermatol. 40, 925-929; and Bai et al. (2003) J. Biol. Chem. 278, 35501-35507). One fraction was found to have activity, and induce a characteristic morphologic change in SVR cells. These changes are similar to what is observed when SVR cells are treated with an EGFR tyrosine kinase inhibitor.

Fraction 5 (0.5 mg) and fraction 6 (1.2 mg) tested positive in the bioassay. TLC comparison of these two fractions revealed the presence of one common UV-active component in both fractions that produced a blue char upon spraying with $H_2SO_4$. Fraction 6 (1.2 mg) was subjected to normal phase-HPLC [1:1 hexanes in $CH_2Cl_2$ (v/v), 1.0 mL min-1, photo-diode-array detection monitored at 254 nm] to obtain 1 (0.7 mg). Compound 1 was identified as carbazole from its NMR and MS spectra and confirmed by direct comparison of authentic sample of carbazole (Aldrich). Carbazole, 2-hydroxycarbazole, 4-hydroxycarbazole and 3,6 dichloro-9-cyclopropylmethylcarbazole were obtained from Sigma-Aldrich Chemical Company (St. Louis, Mo.), and 3-hydroxycarbazole was obtained from David Gibson (University of Iowa) (Resnick et al. (1993) Fems Microbiol. Let. 113, 297-302).

Example 2

Identification of Active Carbazole Derivatives by Inhibition of Endothelial Proliferation Coal tar fractions were tested for their ability to inhibit the proliferation of SVR cells, an established angiogenic bioassay. One fraction was found to have activity, and induce a characteristic morphologic change in SVR cells.

Since carbazole is known to be metabolized by mammals through hydroxylation, hydroxylated and oxidized derivatives of carbazole, including 2,3, and 4 hydroxylated carbazoles, were also tested for their anti-proliferative activity using SVR cells as previously described (Arbiser et al. (1999) Supra; and Bai et al. (2003) Supra). As shown in FIG. 1, carbazole itself had mild antiproliferative activity, while 2-, 3- and 4-hydroxy carbazole had more potent antiproliferative activity. These findings suggest that carbazole and its derivatives have antiangiogenic and antisignalling activities.

Example 3

Drosophila Assay

The epidermal growth factor receptor pathway controls cell fate throughout phylogeny. Binding of secreted ligands to EGFR on the cell surface initiates a cascade of events that ultimately invokes transcriptional changes in the nucleus. Ligand/receptor interactions are of critical importance during Drosophila eye development, as recruitment and differentiation of almost all photoreceptors are dependent on high levels of activation of the EGFR pathway. Binding of activating ligand to EGFR results in a cascade of membranous and cytoplasmic phosphorylation events.

In order to test whether carbazole and its derivatives affect EGFR, the compounds were tested using a novel EGFR assay that is amenable to high throughput screening. Drosophila melanogaster that possess an active EGFR have a distinct eye phenotype, and treatment of mutant Drosophila with carbazole and 4-hydroxycarbazole resulted in correction of the phenotypic defect. Carbazole and 4-hydroxycarbazole had no effect on the normal development of Drosophila embryos.

Example 4

Characterization of Carbazole

To characterize the carbazole isolated from the fraction, NMR studies were performed. The $^1$H NMR, $^1$H-$^1$H COSY, $^{13}$C NMR, DEPT, HMQC and HMBC spectra were recorded on a Varian Unity Inova spectrometer. The $^1$H NMR and $^{13}$C NMR of carbazole (isolated and authentic sample from Aldrich) spectra were recorded on a Bruker DRX 400 spectrometer. Varian NMR spectrometer was operating at 600 MHz for $^1$H and 150 MHz for $^{13}$C and Bruker NMR spectrometer was operating at 400 MHz for $^1$H and 100 MHz for $^{13}$C, respectively. The NMR spectra were recorded running gradients and using residual solvent peaks (7.25 s for $^1$H and 77.2 middle of the triplet for $^{13}$C) as internal references. The electron impact (EI) mass spectra (MS) and gas chromatography (GC) data was acquired on a Hewlett Packard Series II 5890 GC-MS spectrometer. Thin layer chromatography (TLC) analysis were run on Merck TLC plates precoated with $Si_{60}$ $F_{254}$ observed under UV ray at 254 nm and then visualized by spraying with $1:1H_2SO_4$ in EtOH and heating. HPLC separation was carried out on a Waters Millennium system with a 996 photodiode array detector. (Prodigy®. Si-gel, 5 µm, 4.6× 250 mm photodiode-array detection monitored at 254 nm).

Carbazole was identified to be the active ingredient of coal tar. 9H-Carbazole 1 compound was obtained as white amorphous solid; $^1$H NMR ($CDCl_3$, 600 MHz) δ7.23 (2H, ddd, J=8.3, 7.2, 1.2 Hz, H-3, H-6), 7.42 (2H, ddd, J=8.3, 7.8, 1.2 Hz, H-2, H-7), 7.43 (2H, d, J=7.8 Hz, H-1, H-8), 8.08 (2H, d, J=7.2 Hz, H-4, H-5); $^{13}$C NMR ($CDCl_3$, 150 MHz) δ. 110.8 (CH×2, C-1, C-8), 119.7 (CH×2, C-3, C-6), 120.5 (CH×2, C-4, C-5), 123.6 (C×2, C-4a, C-4b), 126.0 (CH×2, C-2, C-7), 139.7 (C×2, C-8a, C-9a); EIMS m/z M+(%) 167 (100), 139 (15), 113 (4), 83 (8).

Example 5

Carbazole Prevents Mononuclear Cell Synthesis of Interleukin 15

In order to determine whether carbazole affected IL-15 production and activation of lymphocytes, cord lymphocytes were activated with polysaccharide (PSK), a well characterized stimulus resulting in IL-15 synthesis.

Cytokine production by mononuclear cells plays an important role in psoriasis. One of the cardinal cytokines involved in the pathogenesis of psoriasis is interleukin-15 (IL-15). IL-15 plays several roles that may be important in psoriasis. First, it causes activation of lymphocyte subsets demonstrated to be pathogenic in psoriasis, including NK like T cells. In addition, IL-15 is angiogenic in vivo. While carbazole had no significant effect on lymphocyte viability, it inhibited production of IL-15.

Figure 2:
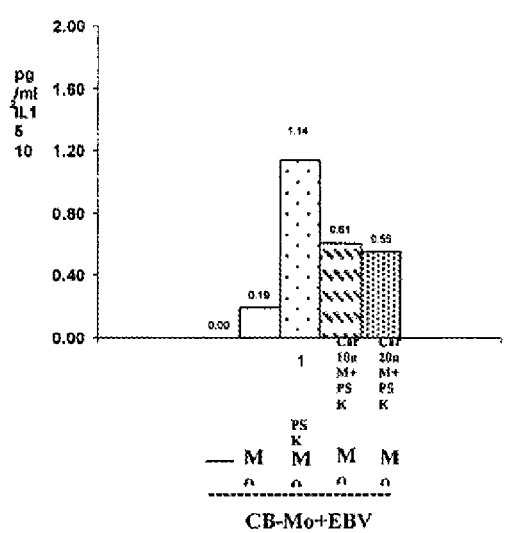
FIG. 2A is a graph showing that is carbazole inhibits T and NK cell activation in peripheral blood mononuclear cells. Production of IL-15 is stimulated by treatment with polysaccharide K (PSK), and is downregulated by carbazole treatment.
FIG. 2B is a graph showing that PSK induces signaling lymphocyte activator molecule associated protein (SAP) expression in lymphocytes, and SAP expression is inhibited by carbazole.
FIG. 2C is a graph showing that cell viability of monocytes is not affected by carbazole.
Figure 2:
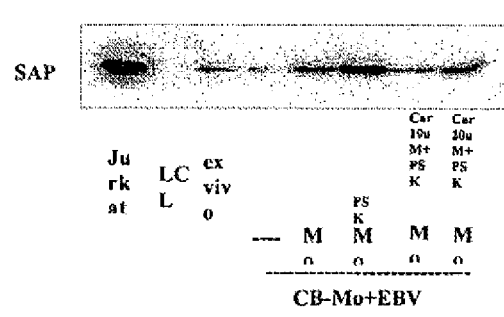
Figure 2:
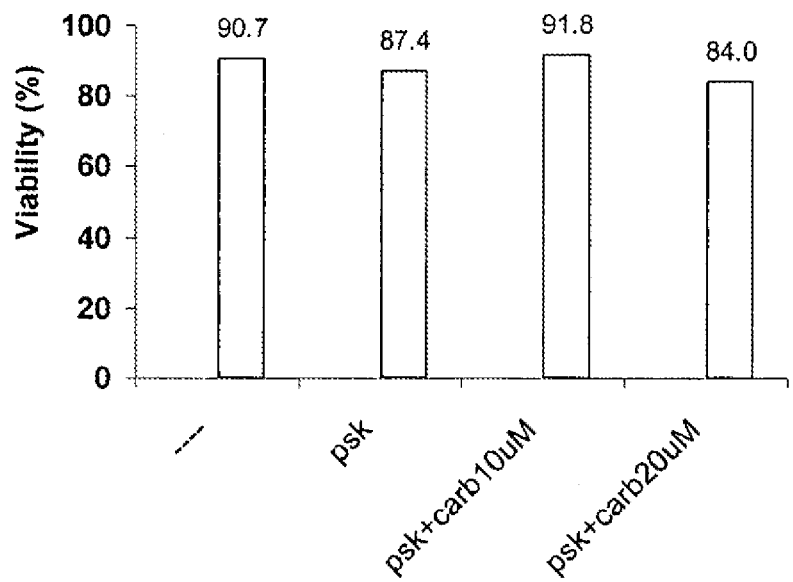

FIG. 2A-C show that carbazole inhibits T and NK cell activation in peripheral blood mononuclear cells. Production of IL-15 is stimulated by treatment with PSK, is downregulated by carbazole treatment (FIG. 2A). PSK induces SAP expression in lymphocytes, and SAP expression is inhibited by carbazole (FIG. 2B), and cell viability of monocytes is not affected by carbazole (FIG. 2C).

Example 6

Carbazole Effects on Inducible Nitric Oxide Synthase (iNOS) Activity

Figure 3A:
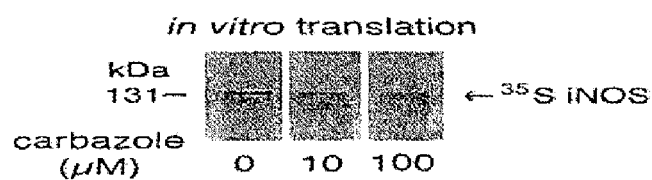
FIG. 3A is a photograph of a membrane showing the effect of carbazole on iNOS translation in vitro.

To investigate the effect of carbazole on iNOS, rabbit reticulocyte-based in vitro coupled transcription/translation system (TnT Quick Coupled transcription/translation system Promega) and iNOS cDNA plasmid, were used to express human iNOS in the presence of 0-100 mM carbazole. Reactions were performed at 30° C. for 90 min. Translation products were separated by SDS/PAGE, and bands, representing $^{35}$S-labeled iNOS, were detected by Phosphoimager (Molecular Dynamics). The data shown in FIG. 3A represent two independent experiments done in duplicates.

For iNOS analysis in cell-lines, human embryonic kidney (HEK) 293 and murine macrophage RAW 264.7 cell lines were purchased from American Type Culture Collection. Cells, and were cultured in manufacturer's recommended media. Each medium was supplemented with 2 mM glutamine, and 10% heat-inactivated fetal bovine serum.

Transfection and stable cell line production of HEK293 cells was performed by cationic lipid-mediated transient transfection using "LipofectAMINE 2000" (Invitrogen) following manufacturer's instructions. Stable cell line expressing iNOS, were produced by using transfection of iNOS cDNA followed by positive colony selection using G418 (Invitrogen) at concentration of 600 µg/ml. iNOS Induction of mouse macrophages RAW264.7, involved incubating the cells with a mixture of mouse interferon (mIFN)-.gamma. (10 u/ml) and LPS (100 ng/ml).

Cell lysis was performed on collected cells. After gently rinsing the cells twice with phosphate-buffered saline, the cell layer was lysed on ice for 30 min in 40 mM Bis-Tris propane buffer, pH 7.7, 150 mM NaCl, 10% glycerol, 1% Triton-X100 in the presence of protease inhibitors (phenylmethylsulfonyl fluoride (1 mM), pepstatin-A (10 µg/ml), leupeptin (10 µg/ml), aprotinin (10 µg/ml), phenanthroline (10 µg/ml), benzamidine HCl (16 µg/ml)) (PharMingen). Lysates were centrifuged (16,000×g, 5 min, 4° C.), and supernatants were stored at −80° C. Total protein concentrations were determined by using a bicinchoninic acid reagent, following the manufacturer's instructions (Pierce).

To examine the proteins expressed in the cells, Western blot analysis was performed. Aliquots of cell lysates (50 mg) were mixed with one third volume of 4× Laemmli sample buffer (200 mM Tris-HCl, pH 6.8/8% SDS/0.004% bromophenol blue/40% glycerol/400 mM DTT), heated at 95° C. for 5 min. Proteins were resolved on SDS/PAGE (NOVEX, San Diego) at 125V and transferred to nitrocellulose membranes for 1 h at 20V by using semidry transfer cell (Bio-Rad). Immunoreactive bands were visualized with the use of enhanced chemiluminescence system (SuperSignal West Pico, Pierce). Images were acquired using a cooled charge-coupled device camera (Eagle Eye II Still Video System, Stratagene).

INOS activity was assayed by assay of nitrite released into the cell growth medium in an iNOS-activity assay. To measure the amount nitrite in the cell medium 100 ml of culture medium was mixed with 100 ml of Griess reagent for 10 min at room temperature, and absorbance at 543 nm was recorded in a microplate reader. Serial dilutions of sodium nitrite were used as standards.

Figure 3B:
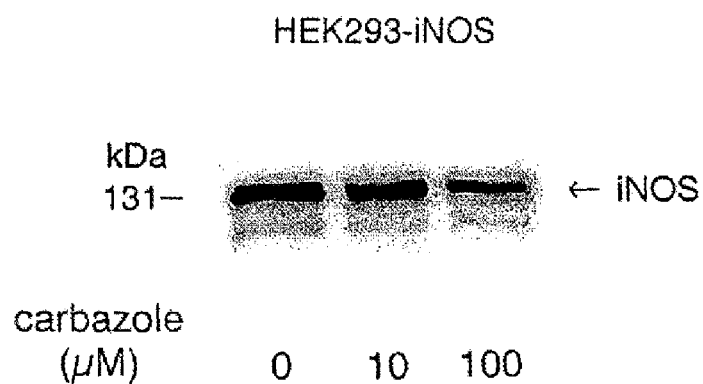
FIG. 3B is a photograph of a membrane showing the effect of carbazole on iNOS expression in cultured cells HEK293.

FIG. 3A shows the in vitro effect of carbazole on iNOS translation in cells. FIG. 3B shows the effect of carbazole on iNOS in cultured HEK293 cells. HEK293 cells, stably expressing iNOS, were incubated for 18 h in the presence of 0-100 mM carbazole. Western blotting of cell lysates (50 µg per lane) was performed by using an anti iNOS antibody. Shown data represent two independent experiments done in duplicates.

Figure 3C:
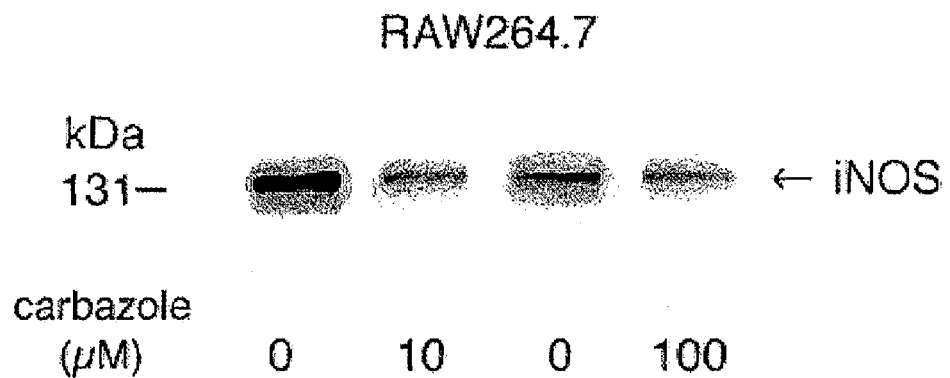
FIG. 3C is a photograph of a membrane showing the effect of carbazole on iNOS expression in cultured cells RAW264.7.
Figure 4:
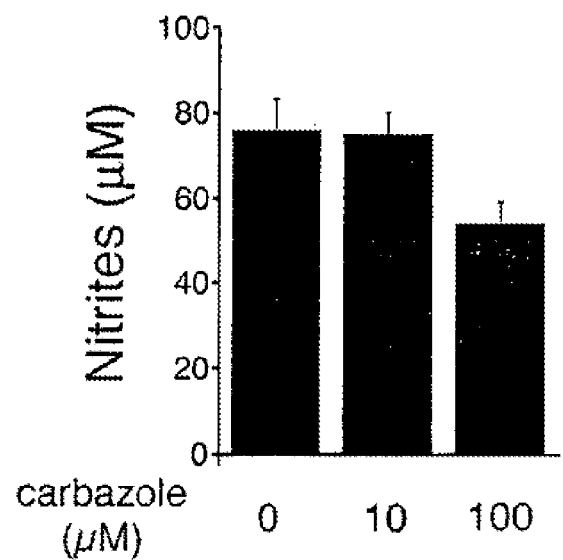
FIG. 4 is a graph showing iNOS activity in RAW264.7 cells treated with carbazole.

FIG. 3C shows the effect of carbazole on iNOS expression in cultured RAW264.7 cells. RAW264.7 cells were stimulated with LPS 10 ng/ml and mIFN-gamma 10 U/ml for 18 hours in the absence or presence of carbazole in concentrations from 10 to 100 mM. Cells were harvested and Western analysis of cell lysates (50 ug per lane) was performed using anti iNOS antibodies. Shown data represent two independent experiments done in duplicates FIG. 4 shows the iNOS activity in RAW264.7 cells treated with carbazole. RAW264.7 cells were stimulated with LPS 100 ng/ml and mIFN-gamma 10 U/ml for 18 hours. During stimulation carbazole was added in concentrations from 0 to 100 mM. iNOS activity was evaluated by measuring nitrite accumulation in culture media (means.+−.SD, n=4). Shown data represent two independent experiments done in duplicates at the following concentrations: 0 µM carbazole-- 76.195 µM nitrites average (SD=7.31); 10 µM carbazole--

75.32 μM nitrites average (SD=4.97); and 100 μM carbazole--54.28 μM nitrites average (SD=4.96).

Example 7

The Effect of Carbazole on Rac Activation

To examine the effects of carbazole in rac activation, HUVECs were grown to confluence and made quiescent in 0.5% fetal bovine serum for overnight. Cells will be pretreated with carbazole, 5 mg/ml) for 1 hr and then stimulated with VEGF (20 ng/ml) for 5 min. Cells were lysed with ice-cold lysis buffer, pH 7.5, containing 25 mmol/liter HEPES, 150 mmol/liter NaCl, 1% IGEPAL CA-630, 0.25% sodium deoxycholate, 10 mmol/liter $MgCl_2$, 10% glycerol, 25 mmol/liter NaF, 1 mmol/liter EDTA, 1 mmol/liter sodium orthovanadate, 10 μg/ml leupeptin, 10 μg/ml aprotinin, and 1 mmol/liter phenylmethylsulfonyl fluoride. Activated (GTP-bound) Rac was affinity-precipitated with p21-activated kinase-1 protein binding domain peptide, which binds only to Rac-GTP and not Rac-GDP.

p21-Activated kinase-1 protein binding domain-agarose (7.5 μg/mg cell lysate, Upstate Biotechnology) was added, and the reaction mixture was gently rocked at 4° C. for 60 min. The agarose beads were collected by pulsing for 5 s in a microcentrifuge at 14,000×g, and the beads were washed three times with 0.5 ml of lysis buffer. The agarose beads were resuspended in 40 μl of 1×SDS sample buffer and boiled for 5 min. The supernatant was separated by SDS-PAGE on a 12% gel, and the proteins were transferred to nitrocellulose membrane. After blocking for 1 h in PBS containing 5% nonfat dry milk and 0.1% Tween 20, the membrane was incubated with anti-Rac antibody (1:1000 dilution, Upstate Biotechnology) overnight. After incubation with the secondary antibody, Rac was detected by enhanced chemiluminescence.

Figure 5:
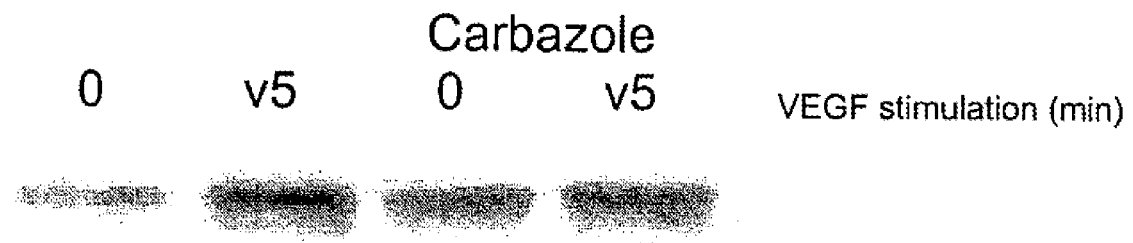
FIG. 5 is a photograph of a membrane showing that carbazole blocks rac activation in response to VEGF.

FIG. 5 shows the effect of carbazole on Rac 1 activity of HUVEC after VEGF stimulation. Carbazole blocks rac activation in response to VEGF to inhibits rac activation in endothelial cells.

Collectively, the data from the above examples shows that treatment of SVR endothelial cells with coal tar fractions resulted in the isolation of a single fraction with antiangiogenic activity. The active antiangiogenic compound in coal tar is carbazole. In addition to antiangiogenic activity, carbazole inhibited the production of inflammatory interleukin-15 by human mononuclear cells.

Potential mechanisms of activity of carbazole include inhibition of epidermal growth factor receptor activation, inhibition of AP-1 activity, and inhibition of proinflammatory cytokine synthesis. It was found that carbazole inhibits the production of interleukin 15 by mononuclear cells, a critical cytokine in psoriasis. The data also shows that carbazole inhibits activity of nitric oxide synthase without affecting levels of enzyme. Given that rac activation has been implicated in both interleukin 15 production and nitric oxide synthase activity, the effect of carbazole on rac activation was examined. It was found that carbazole inhibits rac activation in endothelial cells. Given its antiangiogenic and anti-inflammatory activities, carbazole is likely a major component of the antipsoriatic activity of coal tar. Carbazole and derivatives may be useful in the therapy of human psoriasis.

The invention claimed is:

1. A method for treating skin disorders selected from the group consisting of angiosarcoma, malignant melanoma, hemangioendothelioma, basal cell carcinoma, squamous cell carcinoma, Karposi's sarcoma, hemangioma of childhood, verruca vulgaris, neurofibromatosis, pyogenic granulomas, recessive dystrophic epidermolysis bullosa, venous ulcers, molluscum contagiosum, seborrheic keratosis, Sturge-Weber syndrome, actinic keratosis, acne, rosacea, and eczema, comprising administering a topical composition comprising an effective amount of carbazole, 2-hydroxy carbazole, 3-hydroxy carbazole, or 2,4-dihydroxycarbazole and a pharmaceutically-acceptable carrier or excipient for topical administration
wherein the carbazole, 2-hydroxy carbazole, 3-hydroxy carbazole, or 2,4-dihydroxycarbazole, is at a concentration at least 1% by weight of the composition, with the proviso that the composition is substantially free of non-carbazole components of coal tar extract.

2. The method of claim 1, wherein the formulation comprises a carrier selected from the group consisting of ointments, gels, lotions, sprays, shampoos, powders, foams, and solutions.

3. The method of claim 2, wherein the carbazole is present in the carrier at a concentration of 1-20% by weight.

4. The method of claim 1, wherein the disorder is a skin disorder selected from the group consisting of acne, rosacea, actinic keratosis, and eczema.

5. A method of treating psoriasis, comprising administering a topical composition comprising an effective amount of carbazole, 2-hydroxy carbazole, 3-hydroxy carbazole, or 2,4-dihydroxycarbazole and a pharmaceutically-acceptable carrier or excipient for topical administration
wherein the carbazole, 2-hydroxy carbazole, 3-hydroxy carbazole, or 2,4-dihydroxycarbazole, is at a concentration at least 1% by weight of the composition, with the proviso that the composition is substantially free of non-carbazole components of coal tar extract.

6. The method of claim 5, wherein the formulation comprises a carrier selected from the group consisting of ointments, gels, lotions, sprays, shampoos, powders, foams, and solutions.

7. The method of claim 5, wherein the carbazole is present in the carrier at a concentration of 1-20% by weight.

* * * * *

UNITED STATES PATENT AND TRADEMARK OFFICE
CERTIFICATE OF CORRECTION

PATENT NO. : 9,289,414 B2
APPLICATION NO. : 13/956170
DATED : March 22, 2016
INVENTOR(S) : Jack L. Arbiser It is certified that error appears in the above-identified patent and that said Letters Patent is hereby corrected as shown below:

In the Specification

Please replace Column 1, Lines 18-21 with the below:
--"This invention was made with governmental support under grant number AR047901 awarded by the National Institutes of Health. The government has certain rights in the invention."--

Signed and Sealed this
Seventh Day of March, 2023

Katherine Kelly Vidal
*Director of the United States Patent and Trademark Office*